United States Patent [19]

Franzmair

[11] Patent Number: 4,581,460

[45] Date of Patent: Apr. 8, 1986

[54] SUBSTITUTED 1-BENZOYL-2-PHENYLIMINOIMIDAZOLIDINE DERIVATIVES

[75] Inventor: Rudolf Franzmair, Linz, Austria

[73] Assignee: Chemie Linz Aktiengesellschaft, Linz, Austria

[21] Appl. No.: 611,162

[22] Filed: May 17, 1984

Related U.S. Application Data

[63] Continuation-in-part of Ser. No. 454,553, Dec. 30, 1982, abandoned.

[30] Foreign Application Priority Data

Jan. 7, 1982 [DE] Fed. Rep. of Germany ....... 3200258

[51] Int. Cl.$^4$ .......................................... C07D 233/50
[52] U.S. Cl. ..................................... 548/315; 548/320
[58] Field of Search ......................................... 548/315

[56] References Cited

U.S. PATENT DOCUMENTS

| 3,740,401 | 6/1973 | Stahle et al. | 548/351 |
| 3,850,926 | 11/1974 | Stahle et al. | 548/348 |
| 3,988,345 | 10/1976 | Franzmair | 424/273 R X |
| 3,998,956 | 12/1976 | Stahle et al. | 424/273 R |
| 4,025,607 | 5/1977 | Stahle et al. | 424/273 R |
| 4,036,972 | 7/1977 | Stahle et al. | 424/273 R |
| 4,100,292 | 7/1978 | Stahle et al. | 424/273 R |
| 4,142,051 | 2/1979 | Franzmair | 548/315 |
| 4,262,005 | 4/1981 | McCarthy et al. | 424/273 R |
| 4,389,403 | 6/1983 | May et al. | 424/258 |

FOREIGN PATENT DOCUMENTS

| 687657 | 3/1967 | Belgium | 548/315 |
| 741947 | 5/1970 | Belgium | 548/315 |
| 1044240 | 12/1978 | Canada | 548/315 |
| 1062267 | 9/1979 | Canada | 548/315 |
| 2225160 | 6/1974 | Fed. Rep. of Germany | 548/315 |

Primary Examiner—Richard A. Schwartz
Attorney, Agent, or Firm—Wenderoth, Lind & Ponack

[57] ABSTRACT

Compounds of the formula

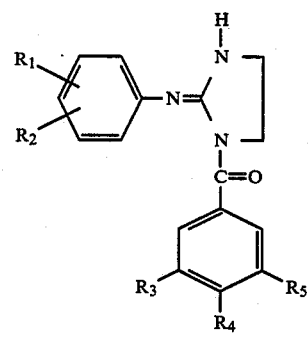

in which $R_1$ and $R_2$ are hydrogen, halogen, methyl or methoxy and $R_3$, $R_4$ and $R_5$ are hydrogen, methyl or an electronegative substituent from the group consisting of halogen, $C_1$ to $C_4$-alkoxy, cyano, nitro or methylsulfonyl, with the proviso that one of the radicals $R_3$ to $R_5$ is always the electronegative substituent of said group, and pharmaceutically acceptable acid addition salts thereof; the compounds as well as the salts are useful as analgesics.

9 Claims, No Drawings

SUBSTITUTED 1-BENZOYL-2-PHENYLIMINOIMIDAZOLIDINE DERIVATIVES

This application is a continuation-in-part of Ser. No. 454,553, Dec. 30, 1982, now abandoned.

FIELD OF THE INVENTION

The present invention relates to new substituted 1-benzoyl-2-phenyliminoimidazolidines, their acid addition salts, process for their preparation and pharmaceutic compositions which contain the new compounds as active ingredient, particularly those having an analgesic effect.

BACKGROUND OF THE INVENTION

It is known from U.S. Pat. No. 4,142,051 of the same inventor that 1-cycloalkenoyl-2-phenyliminoimidazolidines, for example 1-(cyclohex-3-en-1-oyl)-2-(2,6-dichlorophenylimino)-imidazolidine, exhibit analgesic properties and can be used as active ingredients in pharmaceutical products for treating attacks of pain.

On the other hand, U.S. Pat. No. 3,988,345 of the same inventor, benclonidine (1-benzoyl-2-(2,6-dichlorophenylimino)-imidazolidine) and the three isomeric toluyl derivatives of clonidine are described as compounds which are primarily distinguished by a marked antihypertensive effect and which are suitable for the preparation of solutions for injection and, in particular, of medicaments for treating hypertension to be administered orally.

Finally 1-aroyl-2-phenyliminoimidazolidines are known from U.S. Pat. No. 4,389,403 in which the aroyl radical represents an optionally substituted monocyclic or bicyclic heteroaromatic acyl radical. These compounds are also said to have strong hypotensive effects.

SUMMARY OF THE INVENTION

Novel 1-benzoyl-2-phenyliminoimidazolidine derivatives, which have at least one substituent having predominantly electronegative properties on the benzoyl radical, have now been found. Surprisingly, these new compounds have a marked analgesic effect, whilst antihypertensive and central suppressant properties are observed to only a very slight extent.

The invention relates to substituted 1-benzoyl-2-phenyliminoimidazolidine derivative of the formula

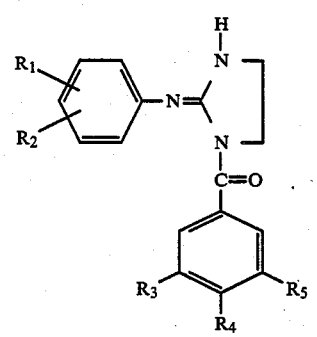

in which $R_1$ and $R_2$, independently of one another, are hydrogen, halogen, the methyl or methoxy group and $R_3$, $R_4$ and $R_5$, independently of one another, are hydrogen, the methyl group or an electronegative substituent from the group consisting of halogen, straight-chain or branched $C_1$ to $C_4$-alkoxy group, the cyano, nitro or methylsulfonyl group, with the proviso that one of the radicals $R_3$ to $R_5$ is always the electronegative substituent of said group and the pharmaceutically acceptable acid addition salts thereof.

DETAILED DESCRIPTION OF THE INVENTION

Advantageous meanings for $R_1$ and $R_2$ are chlorine, bromine, fluorine, methyl or methoxy. Furthermore, it is preferred that $R_1$ and $R_2$ both denote halogen and one of the radicals $R_1$ or $R_2$ is located in the ortho-position on the phenyl radical.

Furthermore, compounds comprised by formula I which are advantageous are those in which $R_3$, $R_4$ or $R_5$ denote the cyano, nitro, methylsulfonyl group, a straight-chain or branched $C_1$ to $C_4$-alkoxy radical, chlorine or fluorine.

Amongst these compounds those are preferred, in which in Formula I $R_1$ and $R_2$ are chlorine or methyl, whereby $R_1$ is located in ortho position of the phenyl nucleus, $R_3$ is $C_1$ to $C_4$ alkoxy, chlorine, fluorine, the cyano or nitro group located in 4- or 3-position of the benzoyl nucleus and $R_4$ and $R_5$ are hydrogen.

In one embodiment of such group of preferred compounds according to the invention $R_1$ is chlorine, $R_3$ is methoxy, ethoxy, i-propoxy or 1-methylpropoxy located in the 4-position of the benzoyl nucleus, $R_2$ is chlorine or methyl and $R_4$ and $R_5$ are hydrogen.

In another embodiment of such group of preferred compounds according to the invention $R_1$ is chlorine or methyl, $R_2$ is chlorine, $R_3$ is the cyano group located in the 3 or 4-position of the benzoyl nucleus and $R_4$ and $R_5$ are hydrogen.

In another embodiment of such group of preferred compounds according to the invention $R_1$ and $R_2$ are chlorine or methyl, $R_3$ is fluorine or chlorine located in the 4-position of the benzoyl nucleus and $R_4$ and $R_5$ are hydrogen.

In another embodiment of such group of preferred compounds according to the invention $R_1$ and $R_2$ are chlorine, $R_3$ is the nitro group located in the 4 position of the benzoyl nucleus and $R_4$ and $R_5$ are hydrogen.

The compounds of the formula I can be manufactured by reacting an aniline derivative of the formula

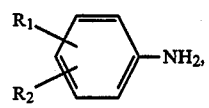

wherein $R_1$ and $R_2$ have the meaning stated above, with a substituted 1-benzoyl-2-imidazolidinone of the general formula

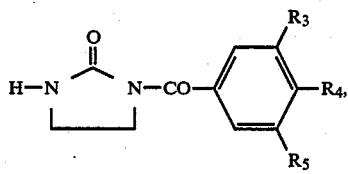

wherein $R_3$ to $R_5$ are defined as in formula I, in the molar ratio 1:1 to 1:1.1 in the presence of at least 2 mole-equivalents of phosphorus oxychloride.

However, it is also possible to obtain the compounds of formula I by reacting a substituted 2-phenyliminoimidazolidine of the formula

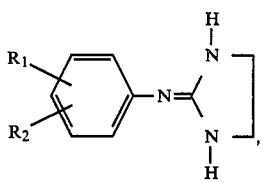

wherein R₁ and R₂ have the meanings stated above, with an active amide of the formula

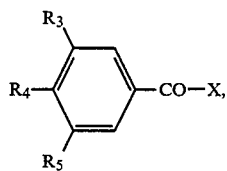

in which R₃ to R₅ are defined as in formula I and X represents the radical of a quasiaromatic five-membered heterocycle having at least 2 nitrogen atoms in the ring, which can optionally be fused with a benzene nucleus, or the radical of the general formula

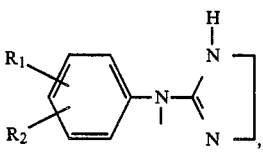

R₁ and R₂ having the meaning given in formula I. This latter process is preferred in most of the cases. The resulting compounds of the formula I can be isolated as free bases or as acid addition salts.

The reaction of the amine of the formula II with a substituted 1-benzoyl-2-imidazolidinone is advantageously carried out at temperatures between room temperature and the boiling point of phosphorus oxychloride, but preferably at temperatures between 50° C. and 80° C. Solvents are not necessary, but can be used. Inert organic solvents are especially suitable, in particular chlorohydrocarbons, such as methylene chloride and chloroform. It is particularly favorable to carry out the reaction in excess phosphorus oxychloride as solvent. The reaction time depends both on the temperature at which the reaction takes place and on the reactivity of the components employed and varies between a few hours and several days.

For working up, the solvent or the excess phosphorus oxychloride is removed as completely as possible in vacuo and the resinous residue, which is a phosphorus oxychloride addition product of the compound of formula I is taken up in a solvent immiscible with water and converted by mild hydrolysis into compounds of the formula I. The mild hydrolysis is as a rule carried out while cooling in ice by slow dropwise addition of basic reagents, for example sodium carbonate solution or dilute sodium hydroxide solution, it being possible for the hydrolysis to be carried out both by direct addition of the hydrolyzing agent to the residue from evaporation and by dissolving the latter in an organic solvent and treating the solution with the alkaline hydrolyzing agent.

A particularly favorable embodiment is provided when the phosphorus oxychloride adduct of the compound of formula I can be obtained in crystalline form by the addition of a suitable solvent. In this case, the crystalline product is suspended in ice-water and subjected to mild hydrolysis as described above. The compounds of formula I according to the invention are then obtained crystalline and of excellent purity.

Some of the 1-benzoyl-2-imidazolidinones of formula III used as starting products have not yet been described. They can be obtained in a known manner by reaction of 2 mole equivalents of 2-imidazolidinone with the appropriate substituted benzoyl chloride in a polar solvent, for example acetonitrile.

Thus, for example, the process for the preparation of 1-(p-methoxybenzoyl)-2-imidazolidinone can be as follows. 34.4 g (0.4 mole) of anhydrous and finely ground 2-imidazolidinone are suspended in 300 ml of anhydrous acetonitrile, and 34.1 g (0.2 mole) of p-methoxybenzoyl chloride, which has been dissolved in 70 ml of anhydrous acetonitrile beforehand, are added dropwise with stirring. To complete the reaction, it is stirred at room temperature for a further 20 hours. The dry residue is subsequently prepared, digested in water, filtered off, washed with water and dried. After recrystallization from isopropanol, 25.17 g (57.2% of theory) of 1-(p-methoxybenzoyl)-2-imidazolidinone, of melting point 173°–176° C., are obtained.

The following compounds were obtained in an analogous manner:

1-(p-nitrobenzoyl)-2-imidazolidinone (78.2% from 90% acetonitrile), melting point 229°–240° C. (decomposition)
1-(m-fluorobenzoyl)-2-imidazolidinone (73.2% from toluene), melting point 160°–163° C.
1-(p-fluorobenzoyl)-2-imidazolidinone (77.9% from toluene), melting point 159°–161° C.
1-(p-chlorobenzoyl)-2-imidazolidinone (69.3% from 80% acetonitrile), melting point 187°–192° C.
1-(3,4,5-trimethoxybenzoyl)-2-imidazolidinone (60.3% from isopropanol), melting point 174°–176° C.
1-(3,4-dimethoxybenzoyl)-2-imidazolidinone (80% from acetonitrile), melting point 181°–183° C.
1-(3,5-dimethoxybenzoyl)-2-imidazolidinone (89.2% from isopropanol), melting point 183°–186° C.
1-(p-cyanobenzoyl)-2-imidazolidinone (91% from isopropanol), melting point 212°–216° C.
2-(p-n-propoxybenzoyl)-2-imidazolidinone (76.5% from acetonitrile), melting point 185°–189° C.

Suitable active amides of formula V are particularly the azolides, it being possible for the radical X in formula V, to be, for example, the radical of an imidazole, pyrazole, 1,2,3-triazole, 1,2,4-triazole, tetrazole, benzimidazole, benzotriazole or their substitution products.

The azolides of formula V can be prepared by known methods from the corresponding substituted benzoyl chloride and 2 equivalents of one of the abovementioned heterocyclic compounds having at least 2 nitrogen atoms in the ring (in this context, compare the contribution by H. A. Staab and W. Rohr in "Synthesen mit heterocyclischen Amiden" (Syntheses with heterocyclic amides) published in W. Foerst, Neuere Methoden der präparativen organischen Chemie (Newer Methods of Preparative Organic Chemistry), Volume V, pages 33 et seq.). Of the azolides, the imidazolides are particularly preferred because of their easy availability. They can be prepared either by the method given above or by reaction of the correspondingly substituted benzoic acid with one equivalent of N,N'-carbonyldiimidazole in an inert solvent.

However, it is not necessary in every case to prepare the azolides of the formula V in a separate step. They can preferably be prepared in situ from one of the azoles mentioned and the appropriate acid chloride and immediately used further. In this process variant, the acyl chloride is reacted with the azole, for example in tetrahydrofuran, filtered off from the azole hydrochloride produced, and the 2-phenyliminoimidazolidine of formula VI is added directly to the solution of the azolide.

It is advantageous to carry out the process such that the substituted 2-phenyliminoimidazolidine is reacted with a 10% excess of azolide at temperatures between room temperature and the boiling point of the solvent, depending on the reactivity of the radical X in the azolide. Aprotic polar and apolar solvents can be used as the solvent. Examples of suitable solvents are aromatic hydrocarbons, such as benzene, xylene or toluene, ethers, such as tetrahydrofuran, diethyl ether or dioxane, esters, such as ethyl acetate, halogenated hydrocarbons, such as methylene chloride, chloroform or carbon tetrachloride, ketones, such as acetone or methyl ethyl ketone and aprotic polar solvents, such as acetonitrile, dimethylformamide or dimethyl sulfoxide. The reaction time depends on the reactivity of the components employed and the reaction temperature chosen and varies from a few hours up to several days.

A favorable variant of the process comprises selecting, as active amide of formula V, a compound in which X has the meaning given in formula VI. This process variant is particularly preferred when the radicals $R_1$ and $R_2$ in the compound of the formula IV to be acylated and in the radical X of the formula VI have the same meaning and occupy the same position on the benzene nucleus. In this embodiment, the 2-phenyliminoimidazolidine of formula IV is employed in significantly less than the stoichiometric amount, advantageously less than half an equivalent, relative to the active amide of formula V, since in the course of acylation, the compound of the formula IV is in fact continuously liberated from the active amide of the formula V. This variant of the process for the preparation of the compounds according to the invention is preferably carried out by boiling the starting materials in an inert aprotic solvent, for example toluene or xylene.

Active amides in which X represents the radical of the formula VI are, according to Belgian Patent Specification No. 741,947, obtainable by reaction of an appropriate substituted 2-phenyliminoimidazolidine of the formula IV with an appropriate substituted benzoyl chloride.

The working up for all process variants is very simple. The residue remaining after the solvent has been evaporated off is digested in a suitable solvent, preferably in water, crystallization usually occurring. the crude product is recrystallized from a suitable solvent.

Furthermore, it is pointed out that the compounds of the formula I according to the invention, just like the 2-phenyliminoimidazolidines of the formula IV, can be present in a tautomeric equilibrium according to the following formulae:

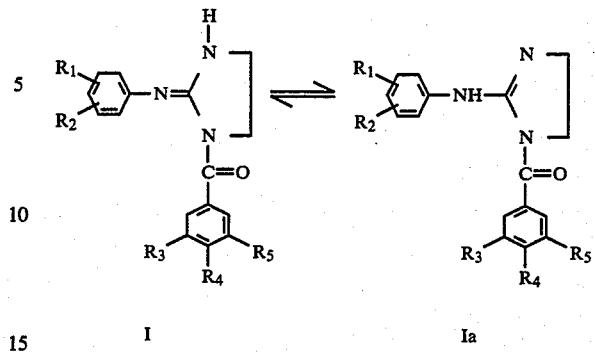

I          Ia

Depending on the process conditions, the final product of the formula I or Ia is obtained either as the free base or as its acid addition salts.

The compounds of the formula I according to the invention having a basic reaction can be converted to the customary manner into their physiologically tolerated acid addition salts. In preparing the acid addition salts, those acids are preferably used which are described in J. Pharm. Sci. 66, 1–16, for the preparation of therapeutically tolerated salts. Examples suitable for salt formation are strong mineral acids, such as hydrochloric, hydrobromic, hydroiodic and hydrofluoric acid, sulfuric acid, phosphoric acid, nitric acid and perchloric acid, aliphatic, alicyclic, aromatic or heterocyclic carboxylic acids or sulfonic acids, such as formic acid, acetic acid, propionic acid, succinic acid, glycolic acid, lactic acid, malic acid, salicylic acid, nicotinic acid, cyclohexylsulfonic acid, methanesulfonic acid or amidosulfonic acids.

The novel compounds of formula I and their acid addition salts have valuable therapeutic properties as analgesics. Due to their ability in low doses to alleviate pain in mammals, they are suitable as drugs having a strong analgesic and a comparatively low or no antihypertensive effect for the treatment of attacks of pain. Most of the substances according to the invention show only a slight or no action on the central nervous system. The analgesic properties of the compounds according to the invention can, inter alia, be demonstrated on the writhing syndrome of the mouse induced by phenyl-p-quinone, which is a standard test for analgesia (Proc. Soc. Explt, Biol. Med. 95, 729, 1957). cl Writhing test 60 minutes after oral application of the test compounds mice were injected intraperitoneally with 0.3 ml of a 0.02% phenyl-p-quinone solution in a alcohol-water mixture (1:25 v/v). After the phenyl-p-quinone injection each mouse was observed during a span of 20 minutes. Mice that did not writhe during the observation period were scored as protected.

The $ED_{50}$ values (antiwrithing potency) were computed according to the method of N. R. Thompsom and C. S. Weil (Biometrics 8, 1952, 51–54, 249–263). The $ED_{50}$ value refers to the dose (mg of test compound/kg of mouse) protecting 50% of the animals from pain in the writhing test.

The $ED_{50}$ obtained with p-cyanobenzoyl-2-(2,6-dichlorophenylimino)-imidazolidine in the writhing test is, for example, only 0.55 mg/kg of mouse.

Examples of the antiwrithing potency ($ED_{50}$) values of compounds according to the invention

| | ED$_{50}$ (mg of test compound/kg of mouse) |
|---|---|
| 1-m-cyanobenzoyl-2-(2,6-dichloro phenylimino)-imidazolidine | 0.25 |
| 1-p-n-propoxybenzoyl-2-(2,6-dichloro-phenylimino)-imidazolidine | 0.46 |
| 1-p-isopropoxybenzoyl-2-(2,6-dichloro-phenylimino)-imidazolidine | 0.54 |
| 1-p-methoxybenzoyl-2-(2,6-dichloro-phenylimino)-imidazolidine | 0.63 |
| 1-p-ethoxybenzoyl-2-(2,6-dichloro-phenylimino)-imidazolidine | 0.98 |
| 1-p-methoxybenzoyl-2-(2,3-dichloro-phenylimino)-imidazolidine | 0.99 |
| 1-(3-methyl-4-nitrobenzoyl)-2-(2,6-dichloro-phenylimino)-imidazolidine | 0.68 |
| 1-p-methylsulfonylbenzoyl-2-(2,6-dichloro-phenylimino)-imidazolidine | 0.75 |
| 1-(3-fluoro-4-methylbenzoyl)-2-(2,6-dichloro-phenylimino)-imidazolidine | 0.50 |
| 1-m-chlorobenzoyl-2-(2,6-dichloro-phenylimino)-imidazolidine | 0.81 |
| 1-p-fluorobenzoyl-2-(2,6-dichloro-phenylimino)-imidazolidine | 0.81 |
| 1-p-fluorobenzoyl-2-(2-chlor-6-methyl-phenylimino)-imidazolidine | 1.0 |
| 1-p-methylsulfonylbenzoyl-2-(2,3-dichloro-phenylimino)-imidazolidine | 1.04 |
| 1-p-fluorobenzoyl-2-(2,3-dichloro-phenylimino)-imidazolidine | 1.15 |
| 1-p-chlorobenzoyl-2-(2,3-dichloro-phenylimino)-imidazolidine | 1.26 |
| 1-p-nitrobenzoyl-2-(2,4-dichlorophenylimino)-imidazolidine | 1.77 |
| 1-m-fluorobenzoyl-2-(2,3-dichloro-phenylimino)-imidazolidine | 2.08 |
| 1-p-chlorobenzoyl-2-(2,4-dichloro-phenylimino)-imidazolidine | 3.54 |
| 1-(3,4-dimethoxybenzoyl)-2-(2,6-dichloro-phenylimino)-imidazolidine | 4.36 |
| 1-(3,4-dimethoxybenzoyl)-2-(2-chloro-6-methylphenylimino)-imidazolidine | 4.42 |
| 1-p-n-butoxybenzoyl-2-(2,3-dichloro-phenylimino-imidazolidine | 4.49 |
| 1-p-fluorobenzoyl-2-(2,5-dichloro-phenylimino)-imidazolidine | 10.0 |

In comparison, the known analgesic Pentazocin ® has a ED$_{50}$ of 168.18 mg/kg in the writhing test and is thus significantly less effective as an analgesic.

Estimates of this antiwrithing potency correlate, at least roughly, with estimates of analgesic potency in man (cf. Taber et al., Inhibition of phenylquinone-induced writhing by narcotic antagonists. Nature London 204: 189, 1964 or Blumberg et al.: Use of writhing test for evaluating analgesic activity of narcotic antagonists, Proc. Soc. Expl. Biol. Med. 118, 763–766, 1965).

The action on the blood pressure was determined, for example, in anaesthetized rats after intravenous administration into the jugular vein, a slight fall in blood pressure being recorded with some of the compounds of the formula I and with others, in turn, a slight rise in blood pressure being recorded, but the change being so minimal that therapeutic utilization would not be possible. The depressant action on the central nervous system, if any, can be detected, for example, by determining the chloral hydrate sleeping time of rats by the method of Laverty and Taylor (Br. J. of Pharmacol. 35 (1969), 253–264).

The novel method of the invention for relieving pain in mammals comprises administering to the mammal a therapeutically effective analgesic amount of at least one compound of the formula I or a pharmaceutically acceptable acid addition salt thereof. The compounds may be administered orally or parenterally. The usual daily dose is 0.1 to 20 mg/kg depending upon the method of administration and the specific compound.

Compounds with very good properties are for example:
1-[p-(1-methylpropoxy)benzoyl]-2-(2,3-dichlorphenylimino)-imidazolidine, 1-[p-(1-methylpropoxy)-benzoyl]-2-(2,6-dichlorophenylimino)-imidazlidiine, 1-p-isopropoxybenzoyl-2-(2,3-dichlorophenylimino)-imidazolidine, 1-p-ethoxybenzoyl-2-(2,3-dichlorophenylimino)-imidazolidine, 1-p-isopropoxybenzoyl-2-(2,6-dichlorophenylimino)-imidazoline, 1-p-chlorobenzoyl-2-(2-chloro-6-methylphenylimino)-imidazolidine, 1-p-chlorobenzoyl-2-(2,6-dichlorophenylimino)-imidazolidine, 1-p-fluorobenzoyl-2-(2-chloro-6-methylphenylimino)-imidazolidine, 1-p-chlorobenzoyl-2-(2,6-dimethylphenylimino)-imidazolidine, 1-p-cyanobenzoyl-2-(2,5-dichlorophenylimino)-imidazolidine, 1-p-cyanobenzoyl-2-(2,4-dichlorophenylimino)-imidazolidine, 1-p-cyanobenzoyl-2-(2-methyl-3-chlorophenylimino)-imidazolidine, 1-m-cyanobenzoyl-2-(2,6-dichlorophenylimino)-imidazolidine and 1-p-nitrobenzoyl-2-(2,6-dichlorophenyliminoimidazolidine.

Particularly preferred compounds are 1-p-cyanobenzoyl-2-(2,6-dichlorophenylimino)-imidazolidine, 1-p-cyanobenzoyl-2-(2,3-dichlorophenylimino)-imidazolidine, 1-p-methoxybenzoyl-2-(2-chloro-6-methylphenylimino)-imidazolidine, 1-p-ethoxybenzoyl-2-(2-chloro-6-methylphenylimino)-imidazolidine, 1-p-methoxybenzoyl-2-(2,3-dichlorophenylimino)-imidazolidine, 1-p-fluorobenzoyl-2-(2,3-dichlorophenylimino)-imidazolidine and 1-p-nitrobenzoyl-2-(2,4-dichlorophenylimino)-imidazolidine and their pharmaceutically acceptable acid addition salts.

The present invention further relates to pharmaceutical compositions which have analgesic effectiveness and which contain one or more compounds of formula I or their pharmaceutically acceptable acid addition salts as the active ingredient. Effective amounts of the compounds according to the invention can be administered to a patient by any one of a variety of methods, for example orally in the form of tablets, capsules, coated tablets, powders, solutions or suspensions, parenterally in the form of sterile solutions or suspensions or intravenously in the form of solutions. The compounds of formula I are in fact effective as free bases, but, for reasons of stability, ease of crystallization, increased solubility and the like, it is possible to formulate and administer them in the form of their pharmaceutically acceptable addition salts. For producing tablets, capsules, coated tablets, suppositories, powders, solutions or suspensions, it is possible to employ the customarily used galenic auxiliaries, vehicles, disintegrants or lubricants or substances to achieve a depot effect.

The following examples illustrate the invention.

EXAMPLE 1

3.98 g (22 mmoles) of 3-methyl-4-nitrobenzoic acid are dissolved in 75 ml of anhydrous tetrahydrofuran, 3.65 g (22 mmoles) of N,N'-carbonyldiimidazole are added and stirred at room temperature for one hour. 4.60 g (20 mmoles) of 2-(2,6-dichlorophenylimino)-imidazolidine, which have been dissolved in 100 ml of absolute tetrahydrofuran beforehand, are added dropwise, with stirring, to this solution and it is allowed to stand at room temperature for 20 hours. The reaction solution is evaporated in vacuo, water is added to the residue and then extracted three times with ethyl acetate. The combined organic phases are washed with water, dried over sodium sulfate, filtered and evaporated. The residue is recrystallized from cyclohexane:isopropanol (1:3) via active charcoal. 5.20 g (66.1% of theory) of 1-(3-methyl-4-nitrobenzoyl)-2-(2,6-dichlorophenylimino)-imidazolidine, having a melting point of 152°–154° C., are thus obtained.

EXAMPLE 2

4.40 g (22 mmoles) of p-methylsulfonylbenzoic acid are dissolved in 70 ml of anhydrous tetrahydrofuran, 3.56 g (22 mmoles) of N,N'-carbonyldiimidazole are added and stirred at room temperature for one hour. A solution of 4.60 g (20 mmoles) of 2-(2,6-dichlorophenylimino)-imidazolidine in 50 ml of anhydrous tetrahydrofuran is added dropwise while stirring further and the mixture is allowed to stand at room temperature for 20 hours. The residue from evaporation is triturated with water, separated off, washed with water, dried and recrystallized from dimethylformamide/water (1:1). 5.15 g (62.5% of theory) of 1-(p-methylsulfonylbenzoyl)-2-(2,6-dichlorophenylimino)-imidazolidine of melting point 240°–244° C. are obtained.

EXAMPLE 3

3.48 g (21 mmoles) of ethoxybenzoic acid are suspended in 100 ml of anhydrous benzene, 3.40 g (21 mmols) of N,N'-carbonyldiimidazole are added and stirred at room temperature for one hour. 4.60 g (20 mmoles) of 2-(2,6-dichlorophenylimino)-imidazolidine are added to the clear solution and it is boiled under reflux for 4 hours. After evaporation, the residue is triturated with 100 ml of water, filtered, washed with water, dried and recrystallized from toluene. 5.90 g (78% of theory) of 1-p-ethoxybenzoyl-2-(2,6-dichlorophenylimino)-imidazolidine of melting point 146°–148° C. are obtained.

EXAMPLE 4

2.88 g (16 mmoles) of p-isopropoxybenzoic acid are dissolved in 30 ml of anhydrous dioxane, 2.59 g (16 mmoles) of N,N'-carbonyldiimidazole are added and allowed to stand at room temperature for 3 hours. To this is added a solution of 3.45 g (15 mmoles) of 2-(2,6-dichlorophenylimino)-imidazolidine and heated under reflux for 2 hours. Working up is as in Example 1 and recrystallization is from benzene/cyclohexane (1:1).

4.45 g (75.7% of theory) of 1-p-isopropoxybenzoyl-2-(2,6-dichlorophenylimino)-imidazolidine of melting point 146°–148° C. are thus obtained.

EXAMPLE 5

1.74 g (11 mmoles) of p-fluorobenzoyl chloride are dissolved in 50 ml of anhydrous tetrahydrofuran, 1.50 g (22 mmoles) of imidazole are added and boiled under reflux for 1 hour. After cooling down to room temperature, the precipitated imidazole hydrochloride is filtered off, the residue from filtration is washed with anhydrous tetrahydofuran, 2.10 g (10 mmoles) of 2-(2-chloro-6-methylphenylimino)-imidazolidine are added to the combined filtrates and heated under reflux for 6 hours. For working up, the solvent is stripped off under reduced pressure and the residue is digested with water, crystallization occurring. The crystals are filtered, washed with water and dried. After recrystallization from isopropanol, 2.75 g (74.3% of theory) of 1-p-fluorobenzoyl-2-(2-chloro-6-methyl-phenylimino)imidazolidine of melting point 143°–145° C. are obtained.

EXAMPLE 6

3.31 g (48 mmoles) of 1,2,4-triazole are dissolved in 80 ml of anhydrous tetrahydrofuran, 4.80 g (24 mmoles) of 3,4-dimethoxybenzoyl chloride are added and stirred at room temperature overnight. To complete reaction, the mixture is also heated under reflux for 2 hours. After cooling down, the precipitated 1,2,4-triazole hydrochloride is filtered off, the residue from filtration is washed with anhydrous tetrahydrofuran, a solution of 4.60 g of 2-(2,6-dichlorophenylimino)-imidazolidine in 50 ml of anhydrous tetrahydrofuran is added to the combined filtrates and left at room temperature for 16 hours.

It is then evaporated, the residue is triturated with water and a little sodium bicarbonate solution, filtered, dried and recrystallized from acetonitrile. 4.61 g (58.46% of theory) of 1-(3,4-dimethoxybenzoyl)-2-(2,6-dichlorophenylimino)-imidazolidine of melting point 201°–204° C. are obtained.

EXAMPLE 7

2.16 g (11 mmoles) of 1-(p-cyanobenzoyl)imidazole and 2.10 g (10 mmoles) of 2-(2-methyl-3-chlorophenylimino)-imidazolidine in 50 ml of anhydrous carbon tetrachloride are heated under reflux for 4 hours. The mixture is then evaporated to dryness and the residue is triturated with 50 ml of water, filtered, washed with water, dried and recrystallized from acetonitrile.

2.64 g (78.1% of theory) of 1-p-cyanobenzoyl-2-(2-methyl-3-chlorophenylimino)-imidazolidine of melting point 224°–228° C. are obtained.

EXAMPLE 8

2.26 g (11 mmoles) of 1-(p-chlorobenzoyl)-imidazole and 1.89 g (10 mmoles) of 2-(2,6-dimethylphenylimino)-imidazolidine are dissolved in 50 ml of anhydrous acetone, left at room temperature for 16 hours and worked up as in Example 6. After recrystallization from isopropanol/cyclohexane 1:15, 2.50 g (76.6% of theory) of 1-p-chlorobenzoyl-2-(2,6-dimethylphenylimino)-imidazolidine of melting point 143°–145° C. are obtained.

EXAMPLE 9

1.89 g (5 mmoles) of 2-[N-(3-methoxy-4-methylbenzoyl)-N-(2,6-dichlorophenyl)-amino]-2-imidazoline and 115 g (0.5 mmole) of 2-(2,6-dichlorophenylimino)-imidazolidine in 30 of anhydrous xylene are maintained under reflux for 21 hours. After cooling down to room temperature and standing for several hours in the cold, 1.17 g (61.9% of theory) of pure 1-(3-methoxy-4-methylbenzoyl)-2-(2,6-dichlorophenylimino)-imidazolidine of melting point 179°–182° C. crystallize out.

EXAMPLE 10

2.16 g (11 mmoles) of 1-(p-cyanobenzoyl)-imidazole and 2.30 g (10 mmoles) of 2-(2,6-dichlorophenylimino)-imidazolidine in 50 ml of anhydrous carbon tetrachloride are heated under reflux for 4 hours. The mixture is then evaporated to dryness and the residue is triturated with 50 ml of water, filtered, washed with water, dried and recrystallized from acetonitrile.

3.15 g (87.69% of theory) of 1-p-cyanobenzoyl-2-(2,6-dichlorophenylimino)-imidazolidine of melting point 208°–210° C. are obtained.

The following compounds where obtained in analogous manner to examples 1–10:

1-p-chlorobenzoyl-2-(2,6-dichlorophenylimino)-imidazolidine, melting point 173°–175° C.

1-p-methoxybenzoyl-2-(2,6-dichlorophenylimino)-imidazolidine, melting point 154°–156° C.

1-p-fluorobenzoyl-2-(2,5-dichlorophenylimino)-imidazolidine, melting point 157°–158° C.

1-(3,4,5-trimethoxybenzoyl)-2-(2,6-dichlorophenylimino)-imidazolidine, melting point 177°–179° C.

1-p-nitrobenzoyl-2-(2,6-dichlorophenylimino)-imidazolidine, melting point 195°–198° C.

1-p-chlorobenzoyl-2-(2,3-dichlorophenylimino)-imidazolidine, melting point 196°–197° C.

1-p-chlorobenzoyl-2-(2,4-dichlorophenylimino)-imidazolidine with the double melting points from acetonitrile of 142°–143° C. and 150°–152° C.

1-m-fluorobenzoyl-2-(2,6-dichlorophenylimino)-imidazolidine, melting point 177°–179° C.

1-p-fluorobenzoyl-2-(2,6-dichlorophenylimino)-imidazolidine, melting point 169°–171° C.

1-(3,4-dimethoxybenzoyl)-2-(2-chloro-6-methylphenylimino)-imidazolidine, melting point 155°–157° C.

1-p-methoxybenzoyl-2-(2-chloro-4-methylphenylimino)-imidazolidine, melting point 180°–182° C.

1-(p-n-propoxybenzoyl)-2-(2,6-dichlorophenylimino)-imidazolidine, melting point 134°–136° C.

1-p-chlorobenzoyl-2-(2,5-dichlorophenylimino)-imidazolidine, melting point 165°–167° C.

1-p-cyanobenzoyl-2-(2,6-dibromophenylimino)-imidazolidine, melting point 224°–227° C.

1-p-cyanobenzoyl-2-(3,4-dichlorophenylimino)-imidazolidine, melting point 173°–175° C.

1-p-nitrobenzoyl-2-(2,3-dichlorophenylimino)-imidazolidine, melting point 210°–211° C.

1-p-fluorobenzoyl-2-(2-methoxyphenylimino)-imidazolidine, melting point 220°–221° C.

1-m-cyanobenzoyl-2-(2,6-dichlorophenylimino)-imidazolidine, melting point 180°–182° C.

1-p-nitrobenzoyl-2-(2,4-dichlorophenylimino)-imidazolidine, melting point 210°–212° C.

1-p-cyanobenzoyl-2-(2,4-dichlorophenylimino)-imidazolidine, melting point 188°–190° C.

1-p-cyanobenzoyl-2-(2,5-dichlorophenylimino)-imidazolidine, melting point 186°–188° C.

1-p-cyanobenzoyl-2-(2-methyl-3-chlorophenylimino)-imidazolidine, melting point 224°–228° C.

1-(p-n-propoxybenzoyl)-2-(2,3-dichlorophenylimino)-imidazolidine, melting point 110°–112° C.

1-p-chlorobenzoyl-2-(2-chloro-6-methylphenylimino)-imidazolidine, melting point 154°–156° C.

1-(3,5-dimethoxybenzoyl)-2-(2,6-dichlorophenylimino)-imidazolidine, melting point 169°–170° C.

1-p-methoxybenzoyl-2-(2-chloro-6-methylphenylimino)-imidazolidine, melting point 156°–157° C.

1-p-ethoxybenzoyl-2-(2-chloro-6-methylphenylimino)-imidazolidine, melting point 140°–142° C.

1-p-ethoxybenzoyl-2-(2,3-dichlorophenylimino)-imidazolidine, melting point 153°–156° C.

1-p-cyanobenzoyl-2-(2,3-dichlorophenylimino)-imidazolidine, melting point 225°–228° C.

1-p-bromobenzoyl-2-(2,6-dichlorophenylimino)-imidazolidine, melting point 176°–178° C.

1-m-fluorobenzoyl-2-(2,3-dichlorophenylimino)-imidazolidine, melting point 141°–142° C.

1-p-methylsulfonylbenzoyl-2-(2,3-dichlorophenylimino)-imidazolidine, melting point 193°–195° C.

1-m-chlorobenzoyl-2-(2,6-dichlorophenylimino)-imidazoline, melting point 152°–154° C.

1-[p-(1-methylpropoxy)-benzoyl]-2-(2,3-dichlorophenylimino)-imidazolidine, melting point 85°–88° C.

1-[p-(1-methylpropoxy)-benzoyl]-2-(2,6-dichlorophenylimino)-imidazolidine, melting point 137°–140° C.

1-p-isopropoxybenzoyl-2-(2,3-dichlorophenylimino)-imidazolidine, melting point 106°–109° C.

1-p-methoxybenzoyl-2-(2,3-dichlorophenylimino)-imidazolidine, melting point 150°–152° C.

1-p-cyanobenzoyl-2-(2-methyl-5-fluorophenylimino)-imidazolidine, melting point 169°–171° C.

1-p-cyanobenzoyl-2-(3,4-dichlorophenylimino)-imidazolidine, melting point 173°–175° C.

1-p-methoxybenzoyl-2-(2,4-dichlorophenylimino)-imidazolidine, melting point 204°–206° C.

1-p-methoxybenzoyl-2-(2,6-dimethylphenylimino)-imidazolidine, melting point 171°–174° C.

1-p-fluorobenzoyl-2-(2,3-dichlorophenylimino)-imidazolidine, melting point 184°–186° C.

1-(p-n-butoxybenzoyl)-2-(2,6-dichlorophenylimino)-imidazolidine, melting point 98°–100° C.

1-p-methoxybenzoyl-2-(2-chloro-6-methylphenylimino)-imidazolidine, melting point 156°–157° C.

What I claim is:

1. A substituted 1-benzoyl-2-phenyliminoimidazolidine derivative of the formula

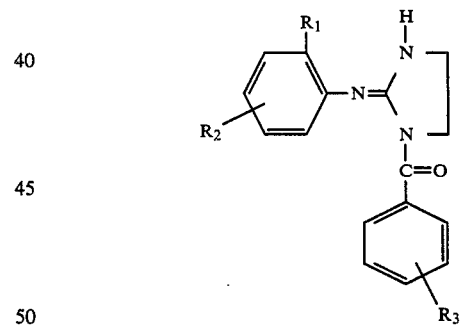

in which $R_1$ is chlorine, $R_2$ is selected from the group consisting of chlorine and methyl and $R_3$ is selected from the group consisting of methoxy, ethoxy, -i-propoxy, 1-methylpropoxy, cyano located in the 4-position of the benzoyl nucleus and cyano located in the 3-position of the benzoyl nucleus, or a pharmaceutically acceptable acid addition salt thereof.

2. A compound according to claim 1, in which $R_3$ is selected from the group consisting of methoxy, ethoxy, i-propoxy and 1-methylpropoxy located in the 4-position of the benzoyl nucleus and $R_1$ and $R_2$ are as defined in claim 1.

3. A compound according to claim 1, in which $R_2$ is chlorine and $R_3$ is selected from the group consisting of cyano located in the 4-position of the benzoyl nucleus and cyano located in the 3-position of the benzoyl nucleus and $R_1$ is as defined in claim 1.

4. The compound according to claim 3 which is 1-p-cyanobenzoyl-2-(2,6-dichlorophenylimino)-imidazolidine or a pharmaceutically acceptable acid addition salt.

5. The compound according to claim 3 which is 1-p-cyanobenzoyl-2-(2,3-dichorophenylimino)-imidazolidine or a pharmaceutically acceptable acid addition salt.

6. The compound according to claim 2 which is 1-p-methoxybenzoyl-2-(2-chloro-6-methylphenylimino)-imidazolidine or a pharmaceutically acceptable acid addition salt.

7. The compound according to claim 2 which is 1-p-ethoxybenzoyl-2-(2-chloro-6-methylphenylimino)-imidazolidine or a pharmaceutically acceptable acid addition salt.

8. The compound according to claim 2 which is 1-p-methoxybenzoyl-2-(2,3-dichlorophenylimino)-imidazolidine or a pharmaceutically acceptable acid addition salt.

9. A compound according to claim 1 in which $R_2$ is located in the 6-position or the 3-position of the phenyl group.

* * * * *